United States Patent [19]

Fernando et al.

[11] Patent Number: 4,836,216
[45] Date of Patent: Jun. 6, 1989

[54] METHOD FOR PREDICTING OPTIMUM TIME FOR INSEMINATION

[75] Inventors: Ranjit S. Fernando; Jennine Regas, both of Aurora, Colo.

[73] Assignee: Zetek, Inc., Aurora, Colo.

[21] Appl. No.: 116,624

[22] Filed: Nov. 3, 1987

Related U.S. Application Data

[60] Continuation-in-part of Ser. No. 43,107, Apr. 27, 1987, which is a division of Ser. No. 713,866, Mar. 20, 1985, Pat. No. 4,685,471.

[51] Int. Cl.$^4$ ................................................ A61B 5/04
[52] U.S. Cl. ...................................... 128/734; 128/738
[58] Field of Search ...................... 128/734, 738, 1 R

[56] References Cited

U.S. PATENT DOCUMENTS

| | | | |
|---|---|---|---|
| 3,844,276 | 10/1971 | McDougall | 128/1 E |
| 3,968,011 | 7/1976 | Manootow et al. | 195/103.5 R |
| 4,224,949 | 9/1980 | Scott et al. | 128/734 |
| 4,685,471 | 8/1987 | Regas et al. | 128/734 |

Primary Examiner—Edward M. Coven
Attorney, Agent, or Firm—Rosen, Dainow & Jacobs

[57] ABSTRACT

In a method for predicting the optimum time for insemination of a human female, for maximum conception probability, the salivary and vaginal resistance of the subject is monitored. The optimum time is predicted as the day on which a rise in vaginal resistance is observed, when such day is within six days of the day of observation of a peak in the salivary resistance, or on the sixth day when no such rise is observed. When no such rise is observed by the sixth day, a second optimum date for insemination is predicted as the day on which the rise in vaginal resistance is observed.

9 Claims, 4 Drawing Sheets

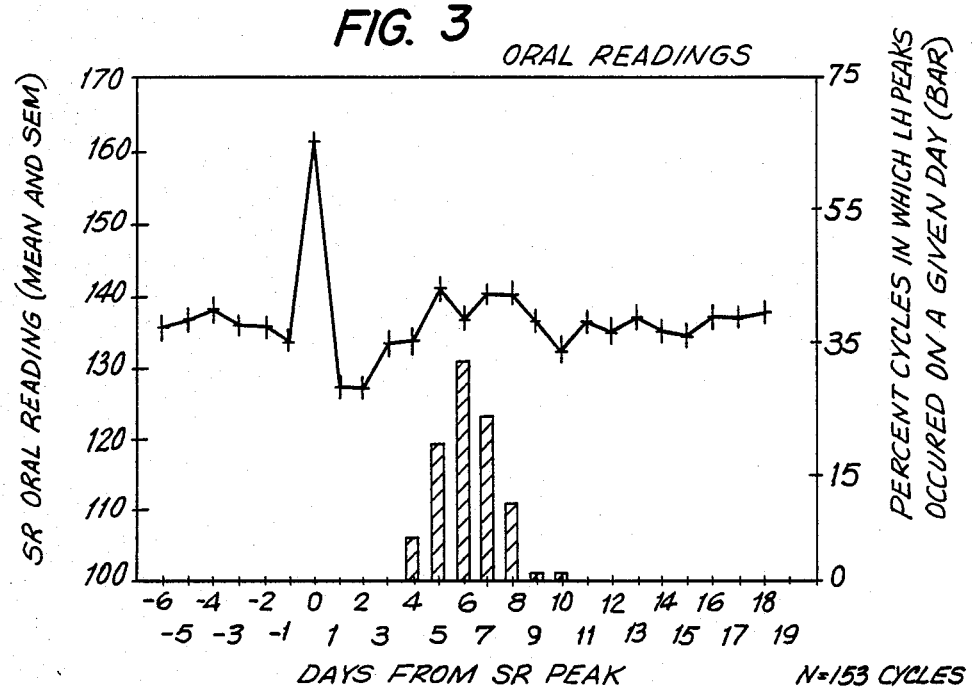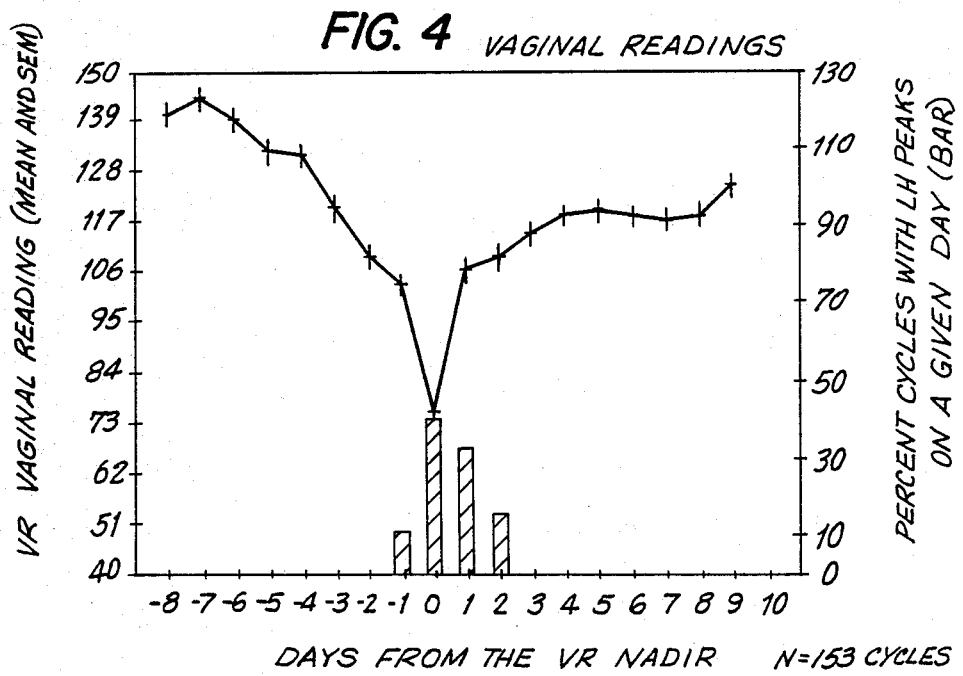

FIG. 5

| CRITERIA FOR TIMING AI | NO. (%) OF CYCLES | NO. (%) WITHIN MCP PERIOD | NO. (%) WITHIN 24 HRS OF LH PEAK | NO. OF AI PER CYCLE |
|---|---|---|---|---|
| GROUP I | 28 (18.3) | 28 (100) | 28 (100) | 1 |
| GROUP II (A) | 74 (48.4) | 72 (97.3) | 69 (93.2) | 1 |
| GROUP II (B) | 51 (33.3) | 50 (98) | 47 (92.2) | 2 |
| OVERALL | 153 (100) | 150 (98) | 144 (94.1) | MEAN 1.3 |

METHOD FOR PREDICTING OPTIMUM TIME FOR INSEMINATION

This application is a continuation-in-part of application Ser. No. 43,107 filed Apr. 27, 1987, which is in turn a division of Ser. No. 713,866, Mar. 20, 1985, now U.S. Pat. No. 4,685,471.

FIELD OF THE INVENTION

1. Background of the Invention

The invention relates to a method for predicting the period of maximum conception probability, especially in human females, and hence the optimum time for insemination, in order to maximize the effectiveness of insemination.

2. Description of the Prior Art

A simple and reliable method for predicting and confirming the time of ovulation has been an important objective of clinicians concerned with the treatment of infertility, since many therapeutic procedures, including artificial insemination (AI) are appropriately done relative to this time. Interpretation of basal body temperature (BBT) charts have been commonly used for this purpose for many years. Well recognized disadvantages of this method are that the technique only provides evidence of ovulation after the fact, and, further, about 10% of ovulatory cycles may have monophasic BBT charts, i.e., they do not indicate ovulation.

Serial assays of luteinizing hormone (LH) carried out at mid-cycle provide an accurate means of short-term (12–16 hour) prediction of ovulation. These tests, when done with serum, are expensive and require venipuncture, which is inconvenient and meets considerable patient resistance.

Recently, home tests for urine LH have become available; these eliminate much of the inconvenience of serum LH tests. However, the requirement for collecting and processing urine samples for up to an hour each, and often at inauspicious times—such as at work—has been reported to be a problem. In order to obtain high accuracy, tests must be performed both morning and evening, leading to further inconvenience and increased expense. Urine LH assays are also subject to problems of dilution created by variation in the patient's fluid intake. Mis-timing of the beginning of the tests at mid-cycle, depending on the number of tests performed, results in missed LH surges.

OBJECTS AND SUMMARY OF THE INVENTION

The principal object of the present invention is to provide a simple, inexpensive, and practical method for predicting the optimum time for insemination, (coital or artificial insemination), to insure the maximum probability of conception in human females.

As disclosed in U.S. Pat. No. 4,685,471, an improved method, hereinafter referred to as the SR-VR method, has been disclosed for predicting ovulation in a human female subject. Briefly stated, in accordance with this method, the salivary (SR) and vaginal mucus (VR) resistances of the subject are monitored, in order to detect determined characteristics and relationships of the resistances over a period of time. In a "normal" cycle, an initial SR peak is noted. This peak coincides with the time of the selection of the dominant follicle—about six or seven days before ovulation. As the follicle develops further, the vaginal readings (VR) decline, beginning about four days before ovulation. This is caused by increasing estradiol ($E_2$) seen at this stage of the follicular phase.

Coinciding approximately with the time of the LH peak, the VR nadir is observed, probably due to the $E_2$ peak which is closely related in time to the LH surge. Next, a VR rise is observed at the time of ovulation. This is related to the effects of declining estrogen and rising progesterone as manifested in the cervical mucus.

In accordance with the invention, it has now been found that the SR-VR method may be employed for predicting the optimum time for insemination, i.e. the time at which the maximum probability of conception occurs. Briefly stated, the optimum day is predicted to be the day on which a rise in vaginal resistance is observed, if it is within six days following the observation of a peak in salivary resistance. If no rise is observed by the sixth day, then the sixth day is predicted as the optimum day. A second optimum day is predicted on the day of the observation of a vaginal resistance rise, if the said rise has not occurred within 24 hours after the said sixth day.

The SR-VR method of prediction in accordance with the invention results in an easy, economical, efficient and accurate method of prediction of the optimum time for insemination, for the greatest probability of conception.

DESCRIPTION OF THE DRAWINGS

In order that the invention may be more clearly understood, it will now be disclosed in greater detail with reference to the accompanying drawings, wherein:

FIG. 3 is a graph showing further oral readings;

FIG. 4 is a graph showing further vaginal readings; and

FIG. 5 is a table illustrating various groups of timing events.

DESCRIPTION OF THE PREFERRED EMBODIMENT

The present invention involves the use of a method, hereinafter called the SR-VR method that has been developed for predicting and accurately identifying the fertile period in the human female, and is disclosed in U.S. Pat. No. 4,685,471.

In accordance with the SR-VR method, a subject is able to predict the onset of her fertile period and the time of ovulation. To this end, the electrical resistance of the subject's saliva is monitored daily, with an instrument designed for that purpose. One suitable instrument, as disclosed in U.S. Pat. No. 4,685,471, is comprised of a housing containing a control circuit, with a digital display, a probe or sensor adapted to be placed on the user's tongue, and a vaginal probe. Oral readings are taken at approximately the same time each day shortly after awakening and prior to putting anything in the mouth, for instance tooth brushing, smoking or breakfast, and other morning activities. To take a reading, excess saliva is swallowed, but with the tongue in moist condition, the sensor is placed on the tongue about 2cm from its tip and held with very light pressure. The salivary resistance (SR) reading is observed on the digital display and is recorded. The readings are plotted, with day-of-cycle on one axis, and the SR values on the other axis, as shown in FIG. 1.

Figure 1:
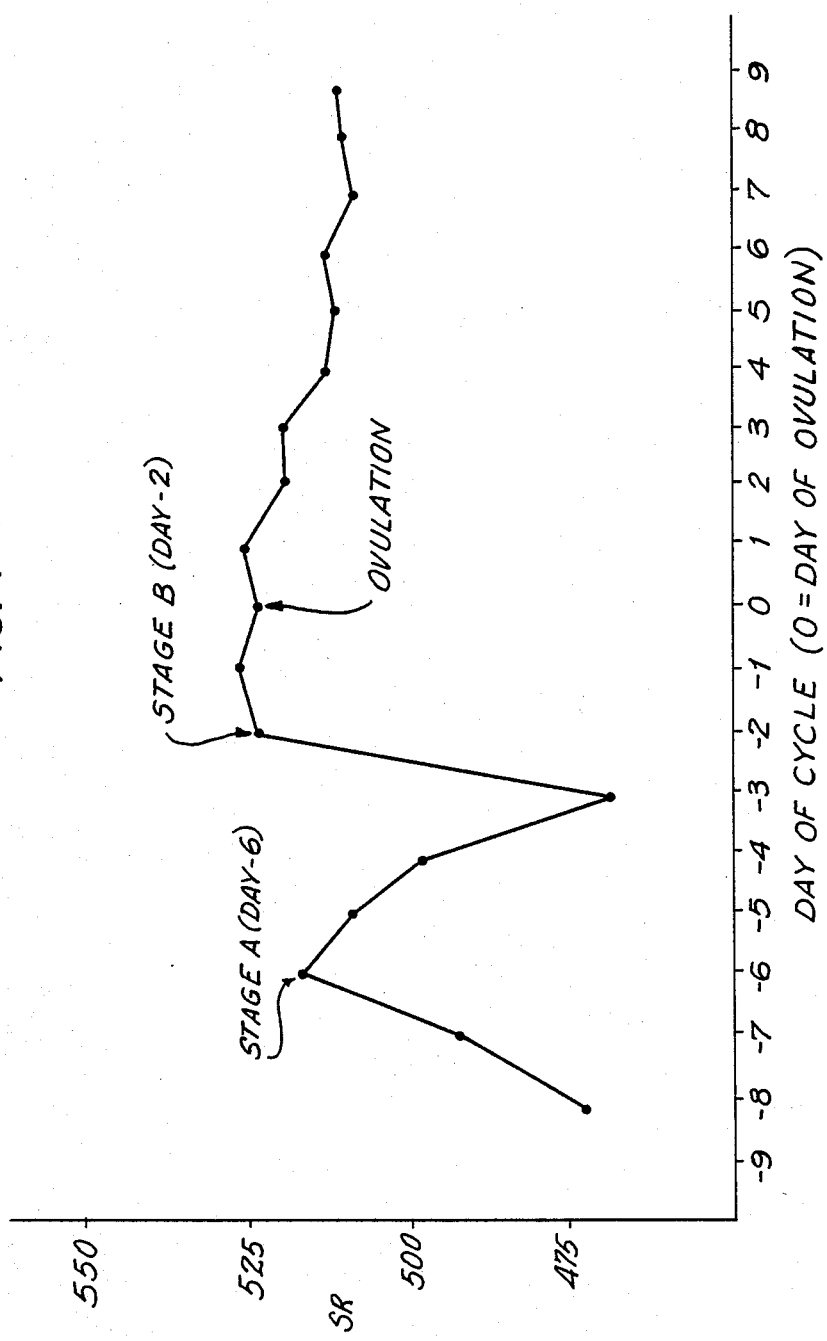
FIG. 1 is a diagram illustrating the pattern of salivary electrical resistance.

When the first peak in SR values (the SR peak) is reached, i.e. when a decline in SR occurs after an initial rise, the first predictive stage has been reached, shown as Stage A in FIG. 1. Regardless of variations in menstrual cycle length, Stage A occurs approximately six days prior to ovulation (on day −6, where day 0 is the day of ovulation). The occurrence of Stage A may vary by approximately ±1 day. Even after accounting for this variation, Stage A occurs prior to the onset of the fertile period, which is assumed to be 72 hours prior to ovulation, and is therefore a good indicator of the imminent fertile phase of the cycle. Thus, if the user wishes to prevent conception, she is made aware of the onset of the fertile period sufficiently in advance so that she may abstain from coitus during its duration.

The next predictive stage, Stage B in the SR values, can be recognized when a sharp increase in readings occurs following a nadir or sharp dip, as shown in FIG. 1. Stage B occurs approximately two days before ovulation, but may vary by ± one day. Stage B is a sign of imminent ovulation, and is useful for identifying the peak of the fertile phase and can be used for timing of coitus or insemination when the user desires to conceive. Patients under the care of a physician may also be scheduled for other evaluations such as post-coital tests, hormone assays, or ultrasonography at this stage. Ovulation will usually occur within two days after Stage B; however, those wishing to avoid conception should abstain from coitus for about four days after Stage B.

While the changes in SR during the menstrual cycle indicate the onset of the fertile period and ovulation, they do not confirm that ovulation has occurred. A method of monitoring the concentration of and interaction between estrogen and progesterone has been developed through their effect both on the ionic concentration and the volume of the cervical mucus. The abrupt decline in estrogen and the subsequent increase in progesterone at the time of ovulation causes marked changes in both ionic concentration and the volume of cervical mucus. These changes are monitored using an intra-vaginal probe that measures the electrical resistance (VR) or conductance of the vaginal mucus, and is sensitive not only to changes in the ionic composition of the mucus but also is sensitive to its volume.

Figure 2:
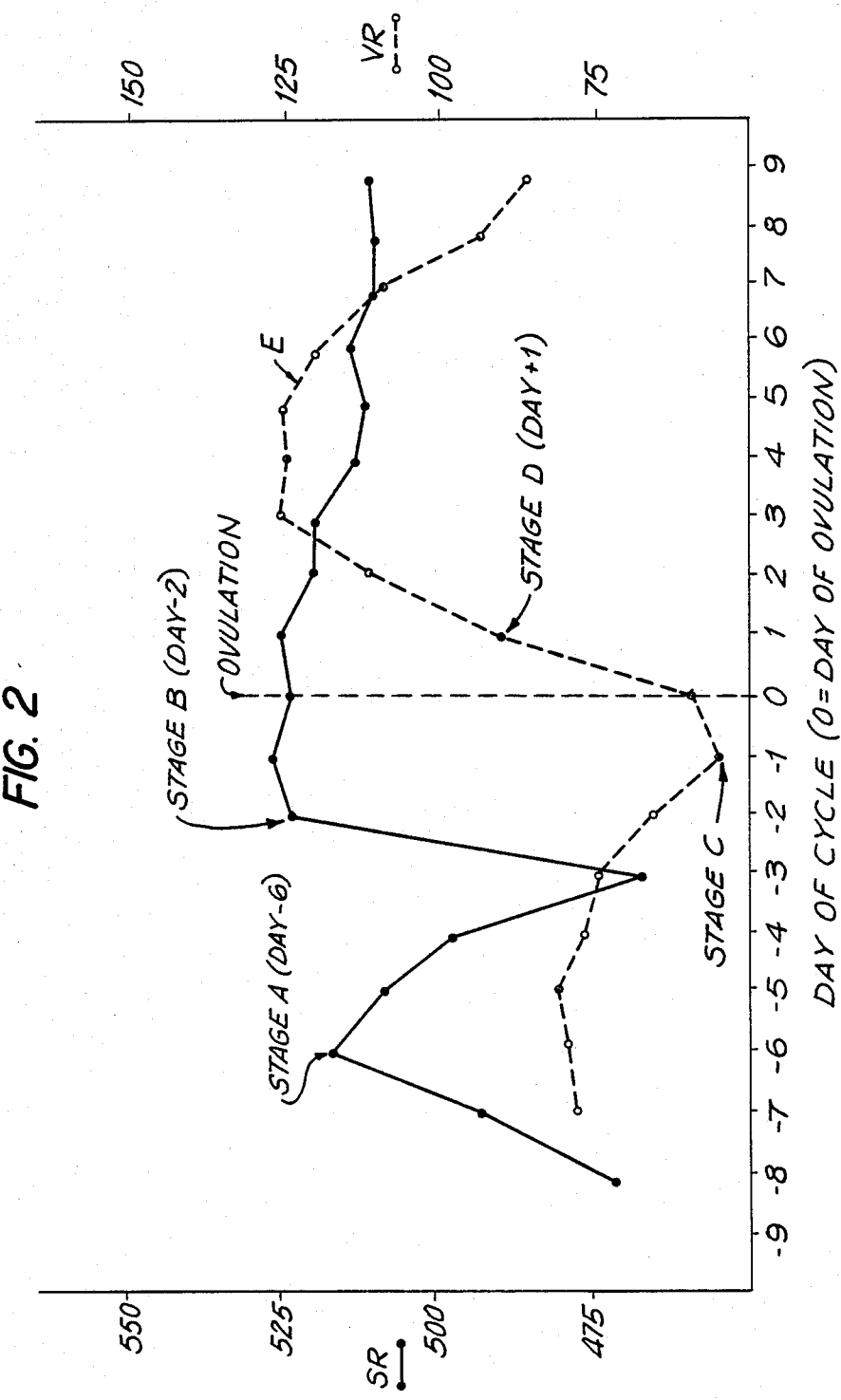
FIG. 2 is a diagram illustrating the pattern of salivary electrical resistance and vaginal electrical resistance.

FIG. 2 illustrates diagrammatically the changes in both SR and VR as related to the menstrual cycle and ovulation. After the initial peak in SR, a marked decrease (Stage C) and increase (Stage D) in VR, indicate respectively that ovulation is imminent (Stage C) and occurring (Stage D). Thus, a reliable indication of ovulation is given in a rapid and simple to use home-test method. By combining the SR and VR readings, the test becomes even more accurate and reliable than when one reading alone is used.

The user is able to predict the onset of the fertile period and the time of ovulation by monitoring changes in both salivary electrical resistance (SR) and vaginal electrical resistance (VR). Determination of SR is carried out as described above; however, when Stage A in the SR is observed or at any earlier time that is after the cessation of menses, the VR readings are obtained in addition to the SR. The VR readings are taken at approximately the same time each day. To obtain a VR reading, a special vaginal probe is connected to the control box used for the electrical resistance measurement, and inserted into the vagina until it rests at the base of the cervix. The VR reading is simply observed on the digital display and recorded. The VR readings are graphed along with the SR values.

The interpretation of the SR values relative to Stage A and B is as described above. Because of the availability of VR measurements, a more precise confirmation of the occurrence of ovulation can be made. During Stage B, the VR reading will be relatively low, reaching a nadir corresponding with the estrogen peak. After ovulation has occurred, the sharp rise in progesterone together with reduced estrogen levels result in a marked elevation in the VR readings. Thus, when the user observes a marked increase in VR that is appropriately related with Stages A and B, it may be taken as a reliable confirmatory indication of ovulation, as shown in FIG. 2. In FIG. 2, the predictive indications of SR are combined with the confirmatory value of VR measurements, thus defining the period of maximum probability of conception, FIG. 2. The use of the VR probe may be discontinued at the end of the said period. Another method is obtained by using electrical conductance or impedance.

Suitable apparatus and methods for obtaining data by the SR-VR method are disclosed and described in U.S. Pat. No. 4,685,4715, the contents of which are incorporated herein by reference.

Research with the SR-VR method has indicated that the signals provided by the method are related to selection of the dominant Graafian follicle, its maturation and collapse.

FIGS. 3 and 4 illustrate the mean oral (salivary) and vaginal resistances, respectively, of a sample of 153 menstrual cycles of normally ovulating women. The cycle day of the midcycle LH peak was determined by serial serum LH assays or urine LH assays. A daily SR and VR reading was taken from each subject in the above described manner. The bar graphs in these figures represent the percentage of menstrual cycles having LH peaks on the respective days.

From the above description, it is apparent that the oral reading shows a peak value about 6 to 7 days prior to the LH peak. This is called herein the "SR" peak. Subsequently, the vaginal reading shows a gradual decline caused by increasing estrogen production from the developing follicle. The low point, or nadir, of the VR trend is usually considered to be the time of ovulation, when a marked increase in VR, the VR rise, is observed. Thus, the SR peak precedes ovulation by about one week, predicting it, while the VR rise is more of a confirmatory signal, resulting from declining estrogens and rising progesterone at this stage of the cycle.

According to the present invention, it has been found that accurate prediction of the optimum time for insemination, using SR-VR readings as above described, is realized in accordance with the following criteria:

Group I. Insemination should be effected on the day on which a VR rise is first observed, if it is observed subsequent to an SR peak, but prior to the sixth day following the day of the observed SR peak. This event indicates imminent ovulation, and thus only one insemination is necessary.

Group II (A). If the VR rise was not observed in accordance with the Group I criteria, then insemination should be effected on the sixth day following the observed SR peak. In accordance with this criterion, only one insemination is necessary, unless the VR Rise is delayed more than 24 hours after this insemination.

Group II (B). If insemination was effected in accordance with Group II (A), and a VR rise is first observed more than one day following the first insemination, then a second insemination should be effected when the VR rise is observed, i.e., when it occurs later than seven days following the SR peak. This group, of course, requires a second insemination The effectiveness of the method in accordance with the invention is illustrated by the results shown in FIG. 5. This table, based on the 153 menstrual cycles that resulted in the data shown in FIGS. 3 and 4, shows that, in 98% of the cases, at least one of a possible maximum of two inseminations would have been timed appropriately. Further, this degree of efficacy would have been attained with 66% of the subjects receiving only a single insemination. Thus, in these examples, correct timing of insemination would be achieved in 98% of the women, with an average of 1.3 inseminations per cycle. It is thus apparent that the method in accordance with the invention, employing SR-VR measurements, provides an accurate prediction of the optimum time for coital or artificial insemination.

The method of the invention, then, provides an accurate, simple and effective technique for predicting the optimum time for insemination, that can be performed by inexperienced subjects with a minimum of expense.

While a limited number of methods embodying the present invention have been described in detail, it should be understood that there is no intention to limit the invention to the specific forms thereof disclosed. On the contrary, the intention is to cover all modifications, alternatives, equivalents, methods, and uses falling within the spirit and scope of the invention as expressed in the appended claims.

What is claimed is:

1. A method for determining the optimum time for insemination, comprising monitoring the SR-VR cycle of a subject daily, and ascertaining the optimum time for insemination as the day on which a VR rise is observed when said day of VR rise is within six days following the day of an SR peak.

2. A method for determining the optimum time for insemination, comprising monitoring the SR-VR cycle of a subject daily, and ascertaining the optimum time for insemination as the sixth day following the day on which an SR peak was observed when a rise in VR has not been observed by said sixth day.

3. The method of claim 2, further comprising predicting a second optimum time for insemination as the day on which a rise in the VR is observed.

4. A method for predicting the optimum time for insemination of a human female subject, comprising monitoring the salivary and vaginal resistances of said subject in a determined menstrual cycle, observing a peak in said salivary resistance, and predicting the optimum time for insemination as the day on which a rise in vaginal resistance is observed when said day is within six days following the day on which said peak was observed.

5. A method for predicting the optimum time for insemination of a human female subject, comprising monitoring the salivary and vaginal resistances of said subject in a determined menstrual cycle, observing a peak in said salivary resistance, and predicting the optimum time for insemination as the sixth day following the observation of said peak, when a rise in vaginal resistance has not been observed by said sixth day.

6. The method of claim 5, further comprising predicting a second optimum time for insemination as the day on which a rise in VR is observed.

7. A method of insemination comprising monitoring the salivary and vaginal resistances of a subject in a determined menstrual cycle, observing a peak in said salivary resistance, and inseminating said subject on the day a rise in vaginal resistance is first observed, when said rise is within six days from the day of observation of said peak.

8. A method of insemination comprising monitoring the salivary and vaginal resistances of said subject in a determined menstrual cycle, observing a peak in said salivary resistance, and inseminating said subject on the sixth day following the day of observation of said peak, when a rise in vaginal resistance has not been observed by said sixth day following said peak.

9. The method of claim 8, further comprising inseminating said subject again on the day a rise in vaginal resistance is observed.

* * * * *